(12) United States Patent
Wang (10) Patent No.: US 11,610,509 B2
(45) Date of Patent: Mar. 21, 2023

(54) FABRICATION OF MICROMODELS FOR CARBONATE RESERVOIRS

(71) Applicant: Saudi Arabian Oil Company, Dhahran (SA)

(72) Inventor: Wei Wang, Quincy, MA (US)

(73) Assignee: Saudi Arabian Oil Company, Dhahran (SA)

( * ) Notice: Subject to any disclaimer, the term of this patent is extended or adjusted under 35 U.S.C. 154(b) by 157 days.

(21) Appl. No.: 17/140,773

(22) Filed: Jan. 4, 2021

(65) Prior Publication Data

US 2022/0215777 A1 Jul. 7, 2022

(51) Int. Cl.
*C01F 11/18* (2006.01)
*G09B 23/10* (2006.01)
*C01F 5/24* (2006.01)
*G09B 23/40* (2006.01)

(52) U.S. Cl.
CPC ............... *G09B 23/10* (2013.01); *C01F 5/24* (2013.01); *C01F 11/18* (2013.01); *G09B 23/40* (2013.01)

(58) Field of Classification Search
CPC ..................................................... C01F 11/18
See application file for complete search history.

(56) References Cited

U.S. PATENT DOCUMENTS

| | | | |
|---|---|---|---|
| 4,882,763 A | 11/1989 | Buchan et al. | |
| 6,226,390 B1 | 5/2001 | Deruyter et al. | |
| 7,373,073 B2 | 5/2008 | Kamp et al. | |
| 7,455,823 B2* | 11/2008 | Murali ............... | C01F 11/187 977/773 |
| 7,520,933 B2 | 4/2009 | Park et al. | |
| 8,062,418 B2 | 11/2011 | Costantz et al. | |
| 9,279,771 B2 | 3/2016 | Aizenberg et al. | |
| 9,873,622 B2 | 1/2018 | Kang et al. | |
| 2006/0120683 A1 | 6/2006 | Kamp et al. | |
| 2009/0174117 A1 | 7/2009 | Winkler et al. | |

FOREIGN PATENT DOCUMENTS

| | | |
|---|---|---|
| CN | 103267825 | 8/2013 |
| CN | 103352255 | 10/2013 |
| CN | 102586873 | 12/2014 |
| CN | 104616350 | 5/2015 |
| EP | 2004573 | 12/2008 |
| EP | 2104082 | 9/2009 |
| EP | 3444028 | 2/2019 |
| FR | 2756046 | 5/1998 |
| FR | 2928484 | 9/2009 |
| KR | 20170131731 | 11/2017 |
| KR | 101852925 | 4/2018 |
| WO | 2007124814 | 11/2007 |
| WO | 2011081681 | 7/2011 |

OTHER PUBLICATIONS

Anbari et al., "Microfluidic Model Porous Media: Fabrication and Applications," Nano Micro Small, Special Issue: Multi-Scale Pores and Channels, 14:18 (1703575), May 2018, 15 pages.
Armstrong et al., "Artificial opal photonic crystals and inverse opal structures—fundamentals and applications from optics to energy storage," Journal of Materials Chemistry C, 3, May 2015, 6109-6143, 35 pages.
Duan et al., "Review article: Fabrication of nanofluidic devices, 7:2 (026501)," Biomicrofluidics, Mar. 2013, 42 pages.
Gerami et al., "Microfluidics for Porous Systems: Fabrication, Microscopy and Applications," Transport in Porous Media, 130, 2019, 277-304, 28 pages.
Hou et al., "Recent advances in colloidal photonic crystal sensors: Materials, structures and analysis methods," Nano Today, 22, 2018, 132-144, 13 pages.
Nge et al., "Advances in Microfluidic Materials, Functions, Integration, and Applications," Chem. Rev., 113:4, Apr. 2013, 2550-2583, 34 pages.
Reese et al., "Synthesis of Highly Charged, Monodisperse Polystyrene Colloidal Particles for the Fabrication of Photonic Crystals," Colloid and Interface Science, 232, 2000, 76-80, 5 pages.
Stein et al., "Design and functionality of colloidal-crystal-templated materials—chemical applications of inverse opals," Chem. Soc. Rev., 42, 2013, 2763-2803, 41 pages.
Florez et al., "Construction of synthetic carbonate plugs: A review and some recent developments." Oil & Gas Science and Technology—Revue d'IFP Energies nouvelles 74, Mar. 2019, 17 pages.
Li et al., "Bioinspired fabrication of 3D ordered macroporous single crystals of calcite from a transient amorphous phase." Angewandte Chemie International Edition 47.13, Mar. 2008, 2388-2393, 6 pages.
Sadakane et al., "Preparation and formation mechanism of three-dimensionally ordered macroporous (3DOM) MgO, MgSO4, CaCO3, and SrCO3, and photonic stop band properties of 3DOM CaCO3." Journal of Solid State Chemistry 184.8, Aug. 2011, 2299-2305, 7 pages.
PCT International Search Report and Written Opinion in International Appln. No. PCT/US2021/065744, dated Apr. 8, 2022, 14 pages.

* cited by examiner

Primary Examiner — Stuart L Hendrickson
(74) Attorney, Agent, or Firm — Fish & Richardson P.C.

(57) ABSTRACT

A carbonate microfluidic model with controllable nanoscale porosity and methods are described. The method for fabricating a carbonate nanofluidic micromodel with controllable nanoscale porosity for studying fluid behaviors in an underground oil-reservoir environment includes: disposing a plurality of polymer spheres into a transparent flow cell; initiating crystallization of the plurality of polymer spheres to form a template with an opal structure; filling the transparent flow cell with a calcium-based solution and a carbonate-based solution to form nanocrystals in voids of the opal structure; and removing the template formed by crystallization of the plurality of polymer spheres from the transparent flow cell leaving an inverse opal structure with a plurality of nanoscale pores and a carbonate surface. The model includes: a transparent flow cell including a first end defining an inlet and a second end defining an outlet; and an inverse opal structure of carbonate inside the transparent flow cell.

19 Claims, 12 Drawing Sheets

FABRICATION OF MICROMODELS FOR CARBONATE RESERVOIRS

TECHNICAL FIELD

The present disclosure generally relates to a method for fabricating micromodels for studying fluid behaviors in an underground oil-reservoir environment, more particularly fabricating nanofluidic micromodels with nanoscale porosity.

BACKGROUND

With the growth of worldwide demand for oil and the decline of the discovery rate of new oil fields, it is important to improve the oil production efficiency of current fields. Many of the world's reservoirs trap about two-thirds of the oil in place where it cannot be recovered by current production methods. To increase oil recovery efficiency, it is important to better understand multiphase fluid behaviors and interactions among oil-water-rock phases in underground oil reservoirs.

A significant proportion of the world's oil reserves are found in carbonate reservoirs. For example, it is estimated that around 70% of oil and 90% of gas reserves are held in carbonate reservoirs in the Middle East. Generally, carbonate rocks are mainly composed of calcite ($CaCO_3$) and dolomite ($CaMg(CO_3)_2$). Based on studies on carbonate reservoir rocks in Arabian Peninsula, at typical reservoir depths, the calcite content is greater than 90 wt. % and even up to 100 wt. % at some depths.

SUMMARY

This specification describes carbonate nanofluidic micromodels that can be used to study fluid behaviors in an underground oil-reservoir environment and methods of making and using these models. The models and methods described in this specification provide a chemical procedure to fabricate a microfluidic chip or cell with nanoscale porosity (i.e. nanofluidic chip or nanofluidic cell), and a surface of calcium carbonate ($CaCO_3$), calcium magnesium carbonate ($CaMg(CO_3)_2$), or both. The nanofluidic micromodels can be used as carbonate micromodels for oil and gas reservoir applications.

In the fabrication process described, commercially available quartz or glass flow cells or chips and polystyrene (PS) colloidal spheres are used. The PS spheres are substantially monodisperse and have a characteristic size between 50 and 1000 nanometers (nm). They are synthesized via a colloidal synthesis method. The PS spheres are assembled within the cell to form a template with a colloidal crystal or photonic crystal structure. After assembly, the void of the template is filled by in situ growth of $CaCO_3$ nanocrystals, simulating calcite, or nanocrystals that includes $CaMg(CO_3)_2$, simulating dolomite. Because the PS spheres surrounded by nanocrystals are densely packed in a near three-dimensional (3D) close-packed colloidal structure, the voids between the spheres filled by nanocrystals form a nanostructured network of calcite or dolomite. When the template of colloidal crystals is removed, an inverse opal structure of calcite or dolomite is created within the cell in which the three-dimensional (3D) void network from a negative replica of template provides pores and channels in the nanoscale range, i.e. nanoscale porosity.

In some aspects, a method for fabricating a carbonate nanofluidic micromodel with controllable nanoscale porosity for studying fluid behaviors in an underground oil-reservoir environment includes: disposing a plurality of polymer spheres into a transparent flow cell; initiating crystallization of the plurality of polymer spheres to form a template with an opal structure; filling the transparent flow cell with a calcium-based solution and a carbonate-based solution to form nanocrystals in voids of the opal structure; growing an inverse opal structure of calcium carbonate or calcium-magnesium carbonate in opal structured template; and removing the template formed by crystallization of the plurality of polymer spheres from the transparent flow cell leaving an inverse opal structure with a plurality of nanoscale pores and a carbonate surface.

Embodiments of the method for fabricating a carbonate nanofluidic model with controllable nanoscale porosity can include one or more of the following features.

In some embodiments, the transparent flow cell has a light path between 0.05 and 1 millimeter (mm) and a volume between 16 and 300 microliters (μL).

In some embodiments, the method also includes synthesizing the plurality of polymer spheres. In some cases, the plurality of polymer spheres has a characteristic size between 50 nanometers (nm) and 1000 nm, and the carbonate nanofluidic model has a resulting controllable porosity between 50 and 1000 nm. In some cases, the method also includes purifying the plurality of polymer spheres in deionized water and redispersing the plurality of polymer spheres in ethanol or in a 1:1 ratio of a water-ethanol mixture.

In some embodiments, the method also includes crystallizing and solidifying the plurality of polymer spheres inside the transparent flow cell by drying them at 60 Celsius (° C.) for 30 minutes.

In some embodiments, the method also includes forming calcium or calcium/magnesium-based solution and injecting the solution into the transparent flow cell. In some cases, the forming of a 1M $Ca^{2+}$ solution includes dissolving a solid $CaCl_2 \cdot 2H_2O$ solution in deionized water as a precursor for the formation of a calcite. In some cases, the forming of a 1M ($Ca^{2+} + Mg^{2+}$) solution was prepared by dissolving $CaCl_2 \cdot 2H_2O$ and $MgCl_2 \cdot 6H_2O$ solutions at 1:1 molar ratio (or other desired $Ca^{2+}/Mg^{2+}$ molar ratios in 1:1 to 1:3.5) in deionized water as a precursor for the formation of a dolomite. In some cases, forming $CaCO_3$ or $CaMg(CO_3)_2$ crystals into the transparent flow cell includes injecting 1M $CO_3^{2-}$ into the transparent flow cell to react with the calcium or calcium/magnesium-based ions. In some cases, forming 1M $CO_3^{2-}$ includes dissolving a $Na_2CO_3$ or $(NH_4)_2CO_3$ solution in deionized water. In some cases, the method also includes filling the voids of the transparent flow cell with the $CaCO_3$ or $CaMg(CO_3)_2$ crystals by injecting the calcium or calcium/magnesium-based solution and the $CO_3^{2-}$ solution into the transparent flow cell alternately for multiple times and drying at 150° C. for 2 hours.

In some embodiments, the method also includes immersing the transparent flow cell into a toluene solution overnight and dissolving the plurality of polymer spheres embedded in calcite or dolomite. In some cases, the method also includes injecting the toluene, a chloroform, or an acetone solution into the transparent flow cell to wash the dissolved plurality of polymer spheres. In some cases, the method also includes forming the inverse opal structure with a plurality of nanoscale pores in calcite or dolomite network by sintering the transparent flow cell at 280° C. for 2 hours.

In some aspects, a carbonate nanofluidic micromodel with nanoscale porosity includes: a transparent flow cell including a first end defining an inlet and a second end defining an outlet; and an inverse opal structure inside the transparent flow cell, the inverse opal structure formed of calcium carbonate with a plurality of nanoscale pores.

Embodiments of the carbonate nanofluidic micromodel with nanoscale porosity can include one or more of the following features.

In some embodiments, the carbonate nanofluidic micromodel has the second end with a filter.

In some embodiments, the transparent flow cell is a demountable quartz cell. In some cases, the transparent flow cell is also a micro-flow cell.

In some embodiments, the inverse opal structure includes a three-dimensional (3D) network with a plurality of connected voids. In some cases, the plurality of connected voids has a controllable nanoscale characteristic size between 50 and 1000 nm. In some cases, the inverse opal structure has surface of calcium carbonate or calcium-magnesium carbonate.

The carbonate nanofluidic cells provide a simple and useful micromodel system for modeling a carbonate reservoir. This approach allows the study of oil-water phase behavior and the interactions between fluids and surfaces, such as rock-fluid interactions, at nanoscale porosities using a small volume of samples and at low cost. The surfaces of nanofluidic cells are optically transparent, allowing interactions between fluids and carbonate or dolomite near the surfaces to be directly visualized by multiple characterization tools, such as advanced spectroscopic and microscopic techniques. The resulting data provides useful information for improved/enhanced oil recovery.

The technology relates to cost-effective chemical methods of fabricating microfluidic chips with precisely controlled porosity at the nanoscale which is smaller than current methods such as lithography. The method enables the conversion of common flow cells to nanofluidic cells. The nanofluidic cells can serve as an effective carbonate micromodel system for studying fluid behaviors in nanoscale porosity. More particularly, this model enables understanding of oil-water phase behavior and rock-fluids interactions at nanoscale. Reservoir micromodels, can be used to mimic the underground oil-reservoir environment for multi-phase flow studies at submicron scales, improved/enhanced oil recovery, and reservoir network mapping. The disclosed micromodels are representation of the properties of a geochemical surface of the carbonate reservoir rocks.

The details of one or more embodiments of these systems and methods are set forth in the accompanying drawings and the description below. Other features, objects, and advantages of these systems and methods will be apparent from the description and drawings, and from the claims.

DETAILED DESCRIPTION

This specification describes carbonate nanofluidic micromodels that can be used to study fluid behaviors in an underground oil-reservoir environment and methods of making and using these models. The models and methods described in this specification provide a chemical procedure to fabricate a microfluidic chip with nanoscale porosity (i.e. nanofluidic chip), and a surface of calcium carbonate ($CaCO_3$), calcium magnesium carbonate ($CaMg(CO_3)_2$), or both. The nanofluidic models can be used as carbonate micromodels for oil and gas reservoir applications.

In the fabrication process described, commercially available quartz or glass flow cells or chips and polystyrene (PS) colloidal spheres are used. The PS spheres are substantially monodisperse and have a characteristic size between 50 and 1000 nanometers (nm). They are synthesized via a colloidal synthesis method. The PS spheres are assembled within the cell to form a template with a colloidal crystal or photonic crystal structure. After assembly, the void of the template is fully filled by in situ growth of $CaCO_3$ nanocrystals, simulating calcite, or a layer of nanocrystals that includes $CaMg(CO_3)_2$, simulating dolomite. Because the PS spheres are densely packed in a near three-dimensional (3D) close-packed colloidal structure, the nanocrystals filled in voids between the spheres form a nanostructured network frame of calcite or dolomite. When the template of colloidal crystals is removed, an inverse opal structure of calcite or dolomite is created within the cell in which the three-dimensional (3D) void network provides pores and channels with controllable sizes in the nanoscale range. The method enables the conversion of common flow cells to nanofluidic cells. The nanofluidic cells can serve as an effective carbonate micromodel system for studying fluid behaviors in nanoscale porosity.

Figure 1:
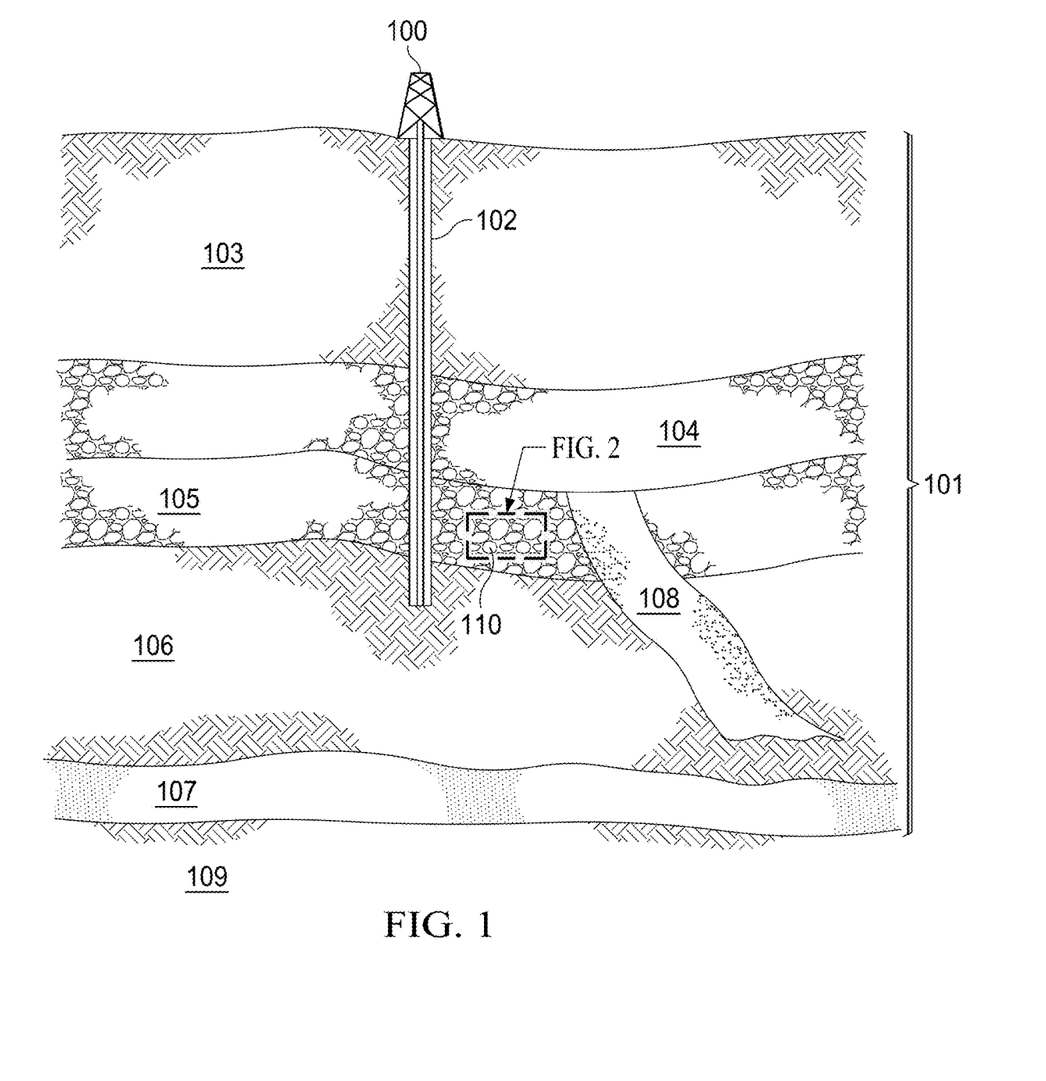
FIG. 1 is a schematic view of a wellbore being drilled through a carbonate reservoir.

FIG. 1 is a schematic view of a wellbore 102 being drilled through a carbonate reservoir 101. The carbonate reservoir 101 includes multiple geological layers 103, 104, 105, 106, 107, 108, 109 which can be rock or salt layers. A drilling rig 100, or other completion equipment, is used to treat the wellbore 102 in the carbonate reservoir 101. This may be done by techniques that create fractures or other openings in the carbonate reservoir 101 to retrieve oil trapped among porous rocks 110. The porosity of a reservoir is the fraction of the total volume of porous media that is occupied by void space, and thus reflects the capacity of reservoir rocks to contain or store fluids.

Figure 2:
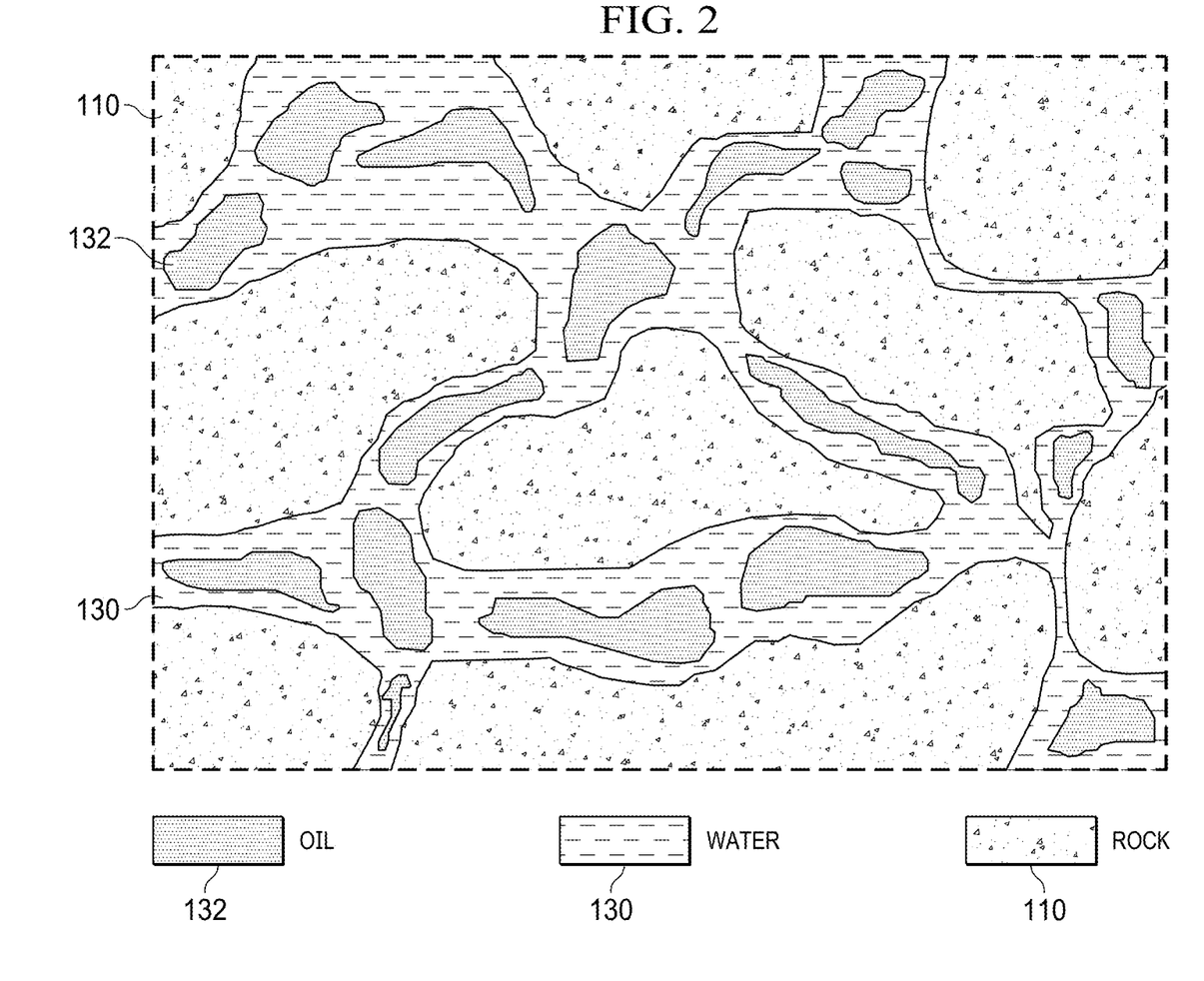
FIG. 2 is a schematic view showing oil trapped among rocks.

FIG. 2 is a schematic view showing oil 132 trapped among rocks 110. In carbonate reservoirs, there can be a high fraction of nanoporosity (e.g., 20+%). However, the majority of the pore space includes micron size pores which provides a microporosity for the overall formation. The nanopores can be 1000 times tighter and smaller than the micropores. Understanding the multiphase flow behavior in the carbonate reservoir is important to determine efficient treatment to improve production. As described, the fabricated nanofluidic chip with controllable porosity and chemical property of the surface can be used as a micromodel system to study multiphase fluid behavior. The usefulness of the nanofluidic chip has been demonstrated for a water flooding experiment for studying oil replacement in nanopore channels, and for an electrokinetic fluid diffusion experiment with dead-end structured nanopores.

Figure 3A:
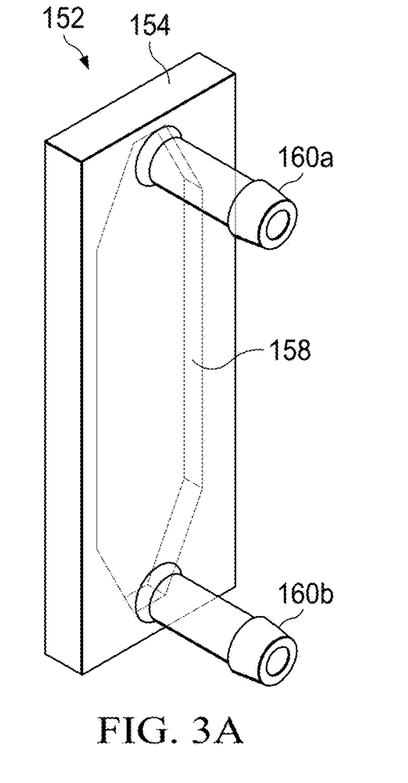
FIGS. 3A-3D are views of an example transparent flow cell and a cell holder.

FIGS. 3A-3D are views of an example transparent flow cell 152 and a cell holder 210. For model fabrication, a commercially available transparent flow cell 152 can be used. The transparent flow cell 152 can be a demountable quartz ($SiO_2$) cell or a micro-flow cell (e.g., Hellma and Starna cells). The transparent flow cell 152 includes a rectangular body 154 with cut 158 in the center that includes an ellipsoid shape with rectangular edges, a top cylindrical extrusion 160a, and a bottom cylindrical extrusion 160b (FIG. 3A). The top cylindrical extrusion 160a defines an inlet and the bottom cylindrical extrusion 160b defines an outlet.

Figure 3B:
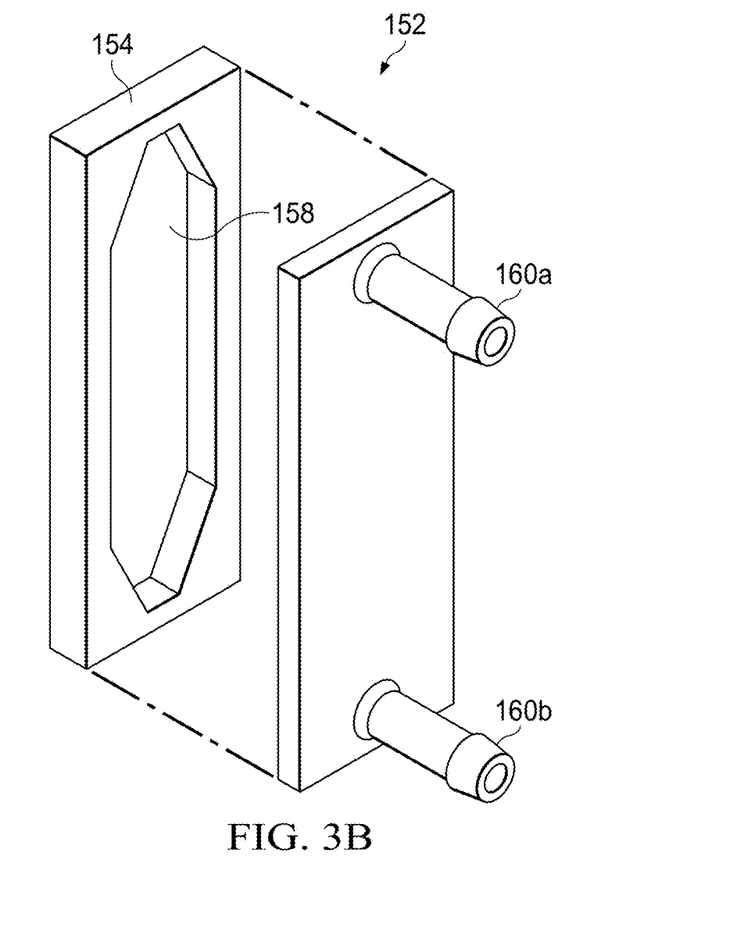
Figure 3C:
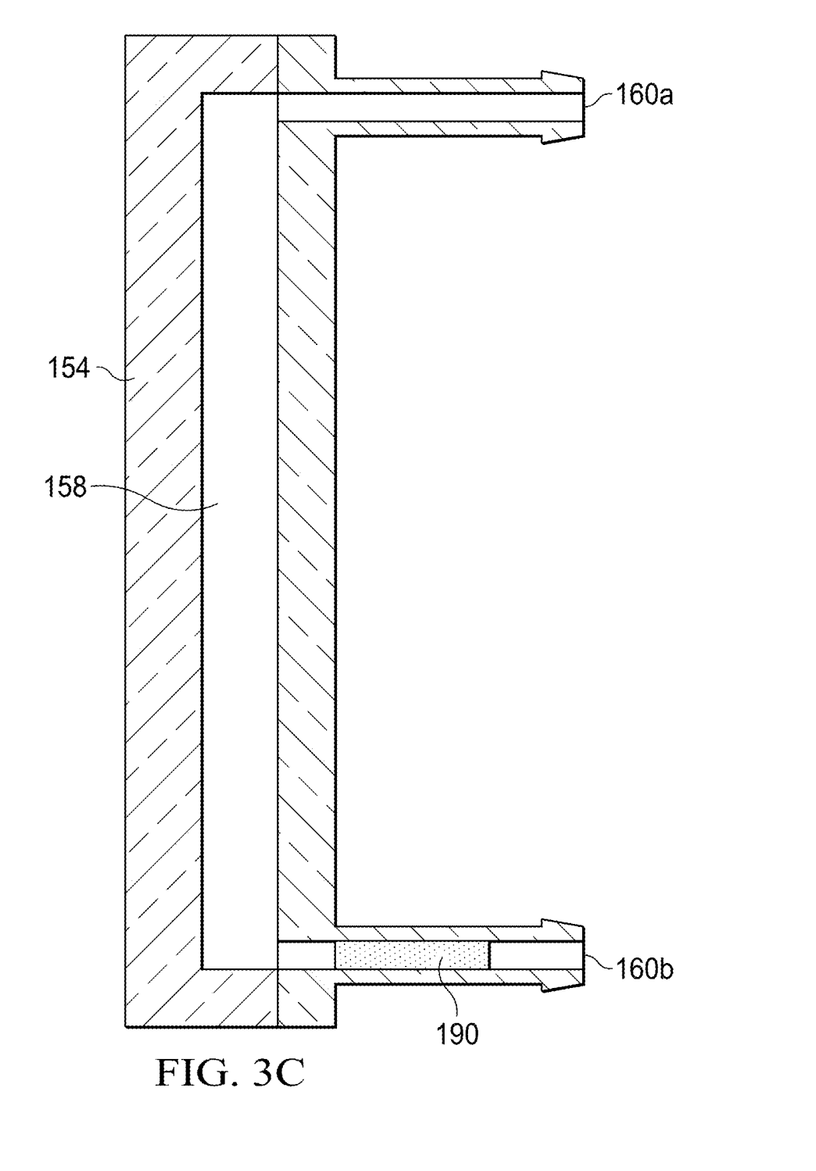
Figure 3D:
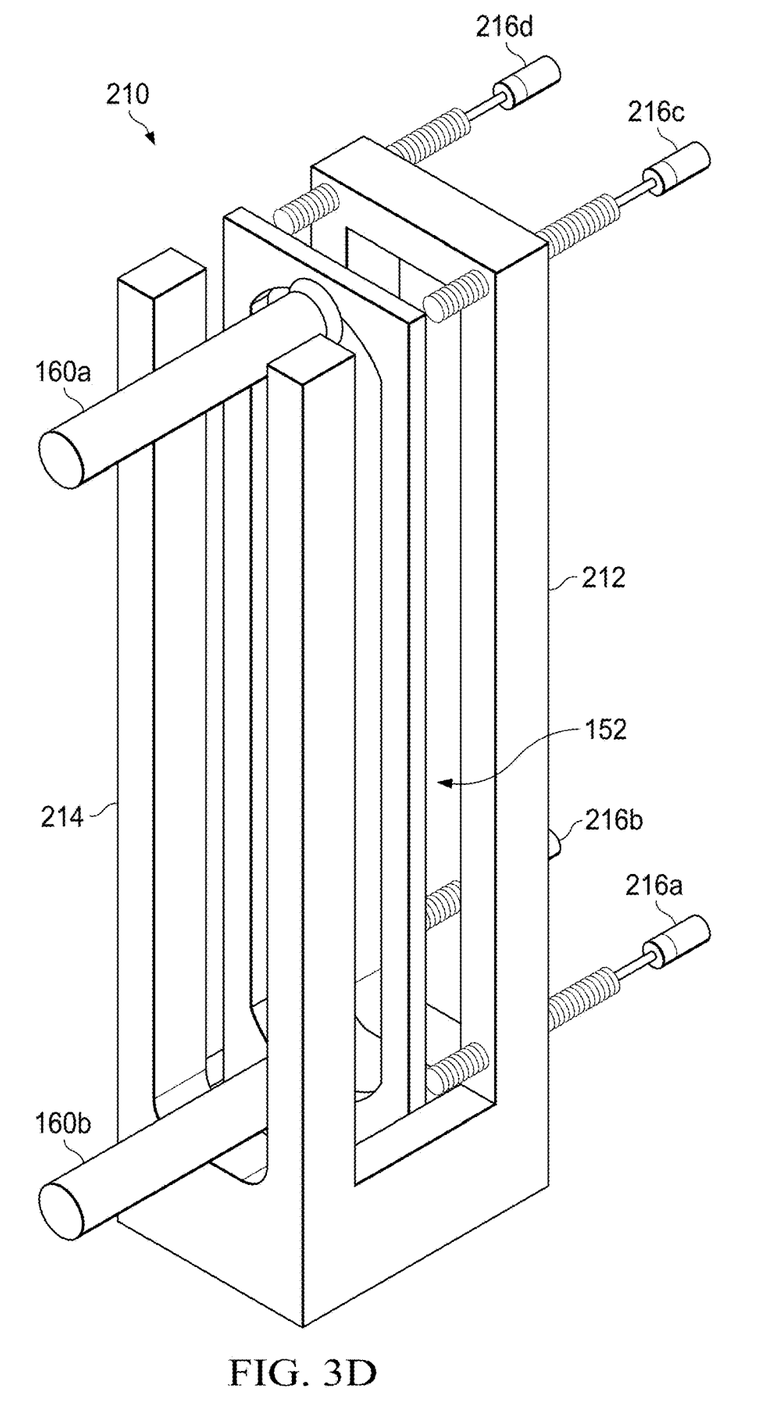

FIG. 3B shows an exploded view of the transparent flow cell 152. FIG. 3C shows a side view of an assembled transparent flow cell 152 that includes a filter 190 inserted into the bottom cylindrical extrusion 160b. The filter 190 has a size of 0.45 micrometers (μm) and retains the PS nanospheres into the cell 152. The transparent flow cell 152 has a lightpath between 0.05 and 1 millimeters (mm) and a volume between 16 and 300 microliters (μL). During laboratory experiments, the transparent flow cell 152 is mounted inside a cell holder 210 (FIG. 3D). The cell holder 210 includes a rectangular elongated body 212 with center cuts 214 on all four sides, and four mounting screws 216a, 216b, 216c, and 216d to hold the flow cell 152 in place. In some embodiments, the flow cell 152 can include various shapes of the flow cell. Using the transparent flow cell a micromodel for a carbonate reservoir is created.

Figures 4A, 4B:
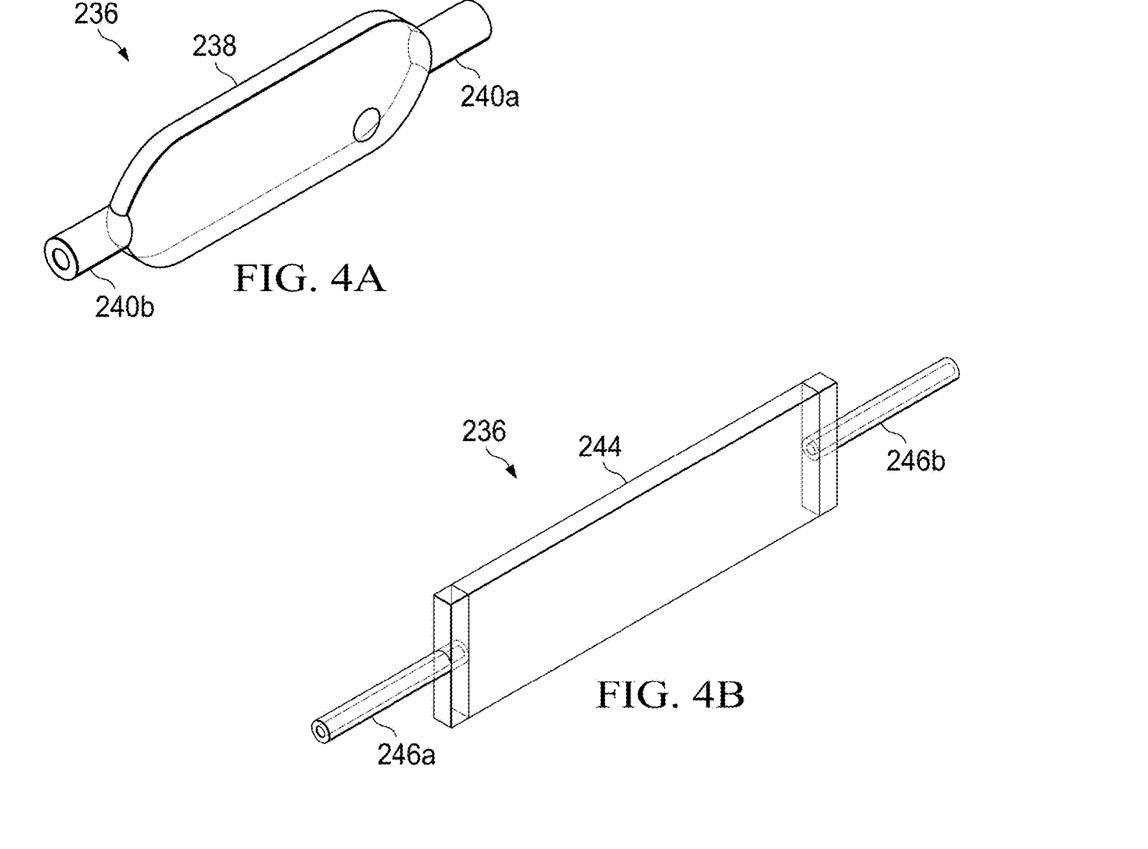
FIGS. 4A-4C are perspective views showing variations of a transparent flow cell.
Figure 4C:
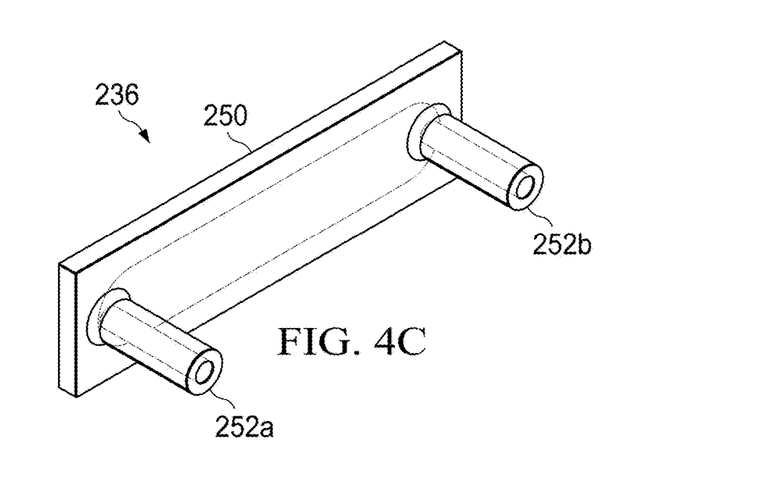

FIGS. 4A-4C are perspective views showing variations of a transparent flow cell. FIG. 4A shows a flow cell 236 with an ellipsoidal body 238 and cylindrical extrusions 240a, 240b on each side of the body 238. FIG. 4B shows a flow cell 242 with a rectangular body 244 and with thin cylindrical extrusions 246a, 246b on each side of the body 244. FIG. 4C shows a flow cell 248 with the same shape as the flow cell 152 described in FIG. 3.

Figure 5:
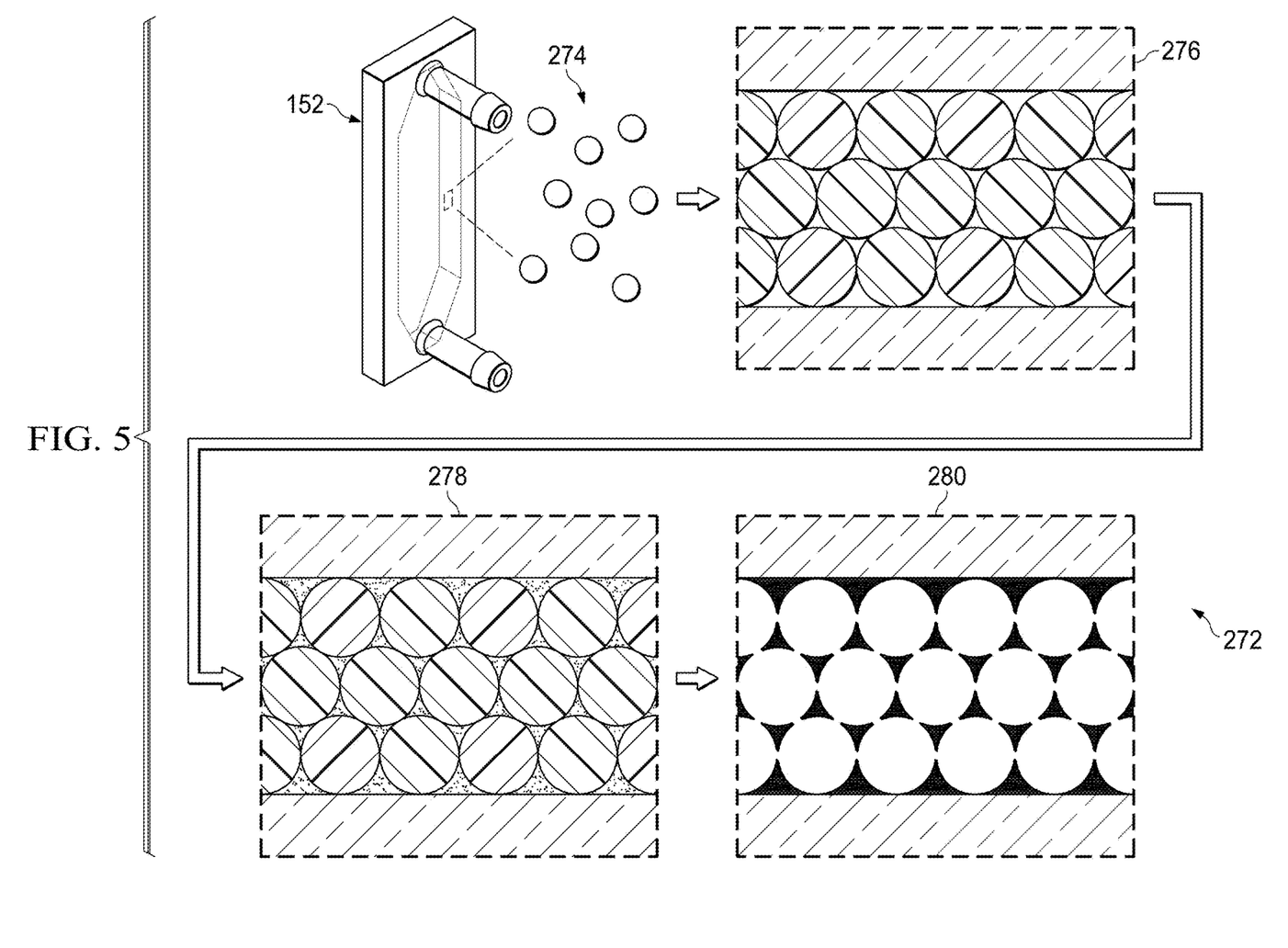
FIG. 5 is a schematic illustrating a method for assembling PS spheres in a microfluidic cell, followed by the growth of calcium carbonate nanocrystals to fill the voids around the spheres, to form a nanofluidic cell.

FIG. 5 is a schematic illustrating a method 272 for assembling PS spheres in a microfluidic chip 274, 276, and growing a calcium carbonate filling 278 surrounding the PS spheres, to form a nanofluidic chip 280. The procedure creates nanoscale pores, or channels, in calcium carbonate ($CaCO_3$) fluidic chips. In an example, the nanofluidic chips are fabricated from commercially available glass or quartz microfluidic chips 152 with two-dimensional (2D) micro-sized channels and porosity. Various microfluidic chips with micrometer porosity (i.e., micropores or microchannels) are commercially available. Next, the monodisperse PS colloidal nanospheres synthesized via a colloidal synthesis method are disposed in the 2D microchannels of the transparent flow cell 152. Then, crystallization is initiated 276 to form a 3D close-packed opal structure within the microchannels or a template. This creates voids between the spheres, and the voids form a 3D connected network of channels. The size of the channels can be controlled in the nanoscale range, or submicron, depending on the sizes of PS spheres used. In this example, the PS spheres have uniform size. To enable the model chemically resemble a carbonate reservoir, a calcium-based solution and a $CO_3^{2-}$-based solution are disposed into the cell and the microchannels alternatively to form calcium carbonate through an in-situ chemical filling process 278. The template is then removed 280 from the transparent flow cell 152 leaving an inverse opal structure of calcium carbonate with a plurality of nanoscale pores.

Figure 6A:
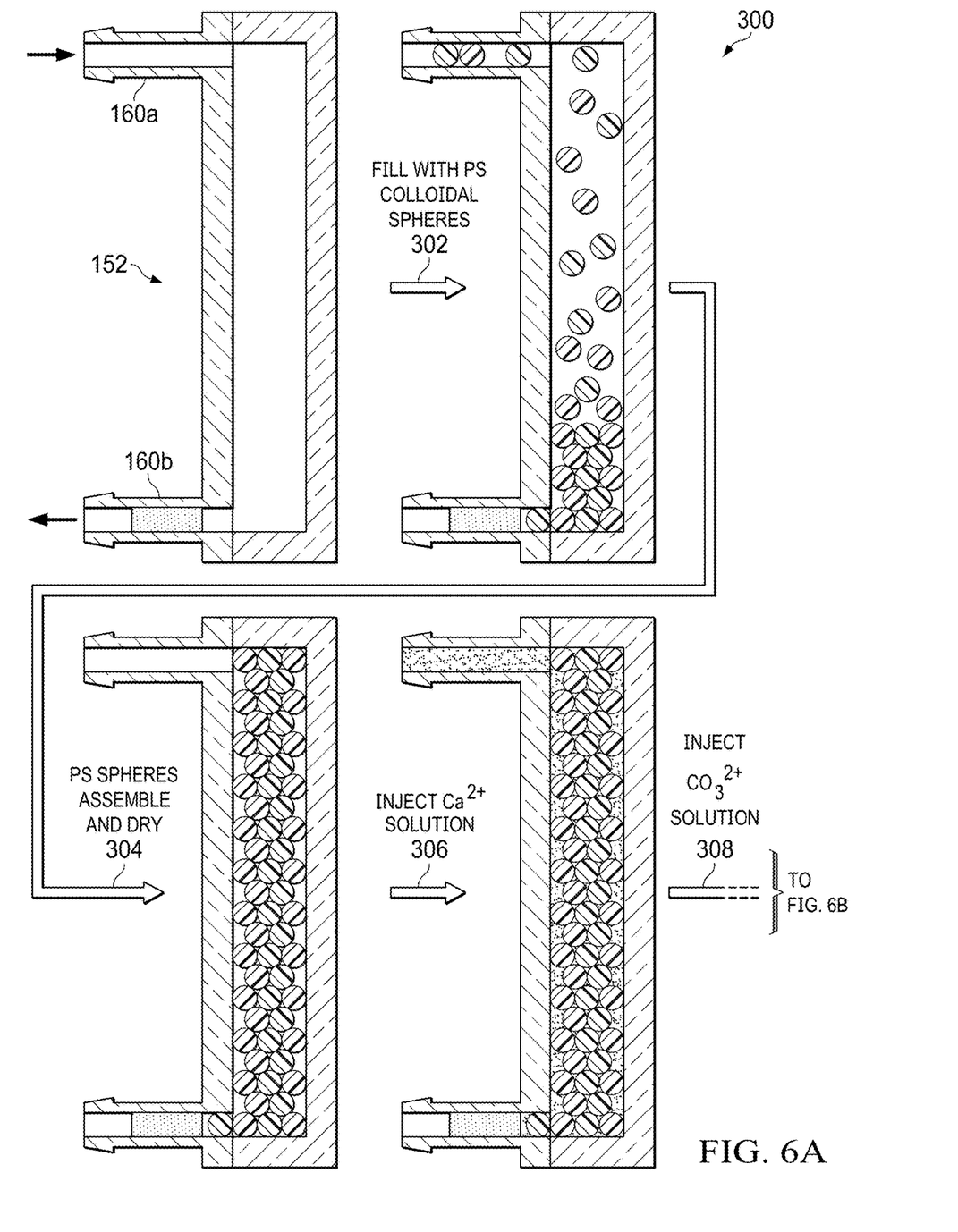
FIGS. 6A and 6B are schematics illustrating a method for fabricating a micromodel with controllable nanoporosity for a carbonate reservoir.
Figure 6B:
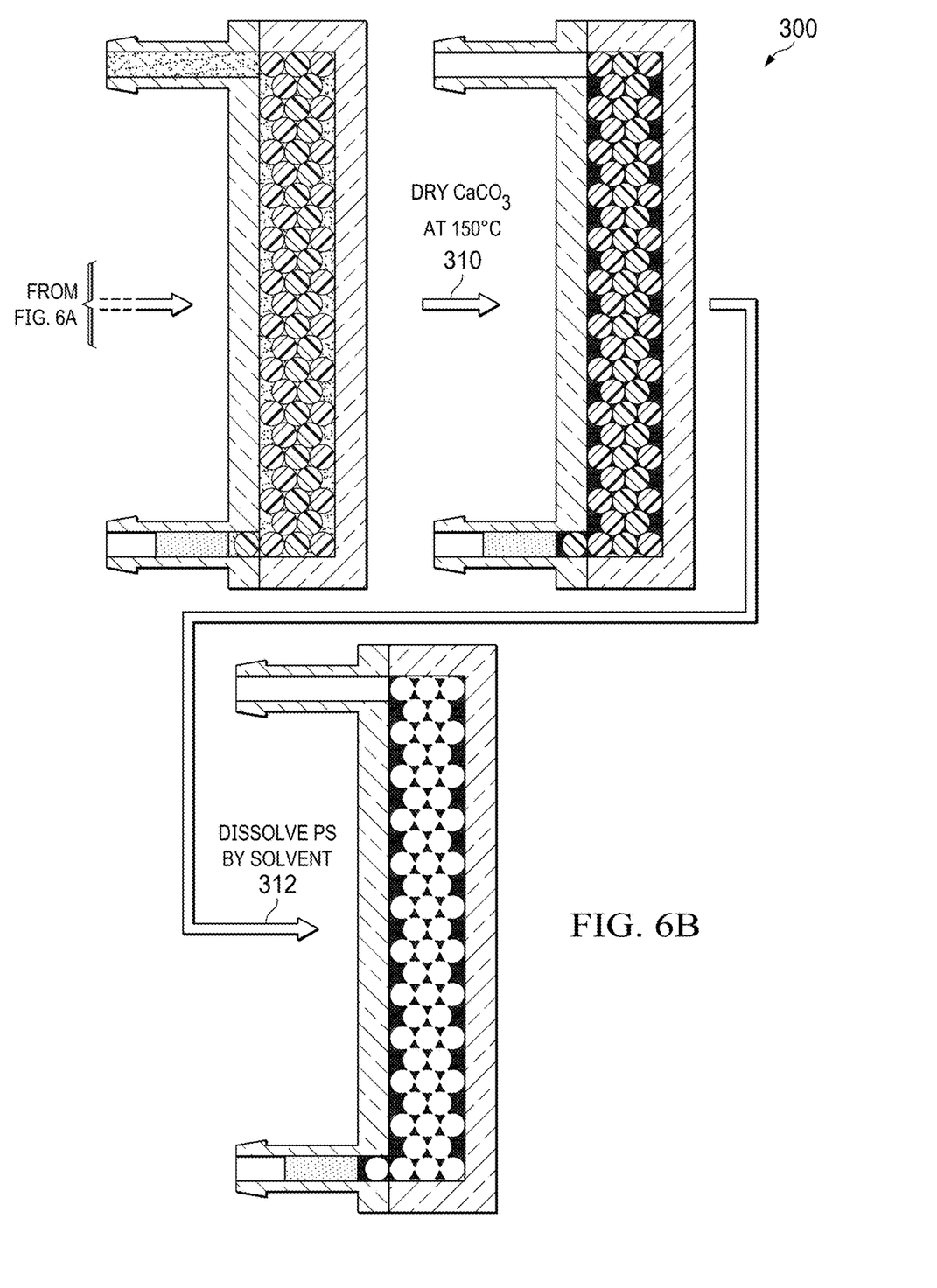

FIGS. 6A and 6B are schematics illustrating a method 300 for fabricating a micromodel with nanoporosity for a carbonate reservoir. The method 300 begins at step 302 with the synthesis of monodisperse PS spheres. The PS spheres were purified in deionized water and redispersed in ethanol or a 1:1 ratio of a water-ethanol mixture. The PS suspension between 2 and 10 wt. % concentration was disposed in the transparent flow cell 152. At step 304, the spheres are assembled in the transparent flow cell 152 to form colloidal crystals. Then nitrogen flow is injected to dry the colloidal crystals and additionally dry them at a temperature of 60 Celsius (° C.) for 30 minutes. At step 306, calcite crystals $Ca^{2+}$ are injected into the transparent flow cell 152. A 1M $Ca^{2+}$ solution is prepared by dissolving solid calcium chloride ($CaCl_2.2H_2O$) in deionized water ($H_2O$) as a precursor for the formation of calcite, and 1M ($Ca^{2+}+Mg^{2+}$) solution is prepared by dissolving $CaCl_2.2H_2O$ and magnesium chloride ($MgCl_2.6H_2O$) at 1:1 molar ratio in deionized $H_2O$ as a precursor for the formation of dolomite. The $Ca^{2+}$ or ($Ca^{2+}+Mg^{2+}$) solution is injected to the cell to fill the voids around the colloidal crystals. At step 308, $CO_3^{2-}$ is injected into the transparent flow cell 152. A 1M $CO_3^{2-}$ solution is prepared by dissolving sodium carbonate ($Na_2CO_3$) or ammonium carbonate (($NH_4)_2CO_3$) in deionized $H_2O$. The $CO_3^{2-}$ solution is injected to the cell to react with the $Ca^{2+}$ or ($Ca^{2+}+Mg^{2+}$) ions, and form in-situ $CaCO_3$ or CaMg $(CO_3)_2$ crystals through the net reactions:

$$Ca^{2+}+CO_3^{2-}\rightarrow CaCO_3\downarrow$$

$$Ca^{2+}+Mg^{2+}+2CO_3^{2-}\rightarrow CaMg(CO_3)_2\downarrow$$

This process of $CaCO_3$ or $CaMg(CO_3)_2$ formation is repeated multiple times until fully filling all the voids around the spheres. The composition may be used to adjust the surface properties to more closely match the chemical composition of a particular carbonate reservoir. For example, other elements may also be included in the solutions to form the thin layer, including, for example, aluminum, silicon, zinc, iron, copper, manganese, titanium, vanadium, or other elements, or combinations of elements, which may be found in target reservoirs. In this example, growing calcium carbonate nanocrystals around the PS spheres forms a microfluidic model to mimic the properties of a calcium carbonate reservoir. At step 310, the cell is dried at 150° C. for 2 hours to solidify the network of $CaCO_3$ or CaMg $(CO_3)_2$. At step 312, the cell 152 is immersed in toluene in a closed container overnight to dissolve the PS colloidal crystal, and then toluene, chloroform, or acetone is injected into the cell 152 to wash the dissolved PS spheres. In the end, the cell 152 with built negative $CaCO_3$ or $CaMg(CO_3)_2$ replica of PS colloidal crystal is sintered at a temperature of 280° C. for 2 hours.

Figure 7A:
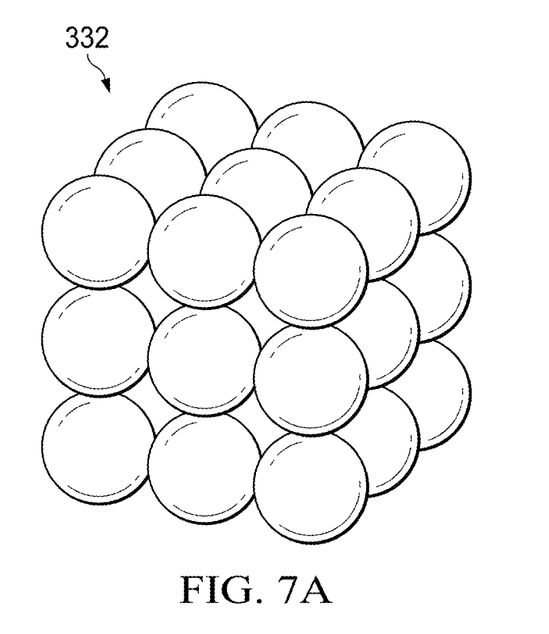
FIGS. 7A-7B are schematics of simple cubic packing opal and inverse opal structure, respectively.
Figure 7B:
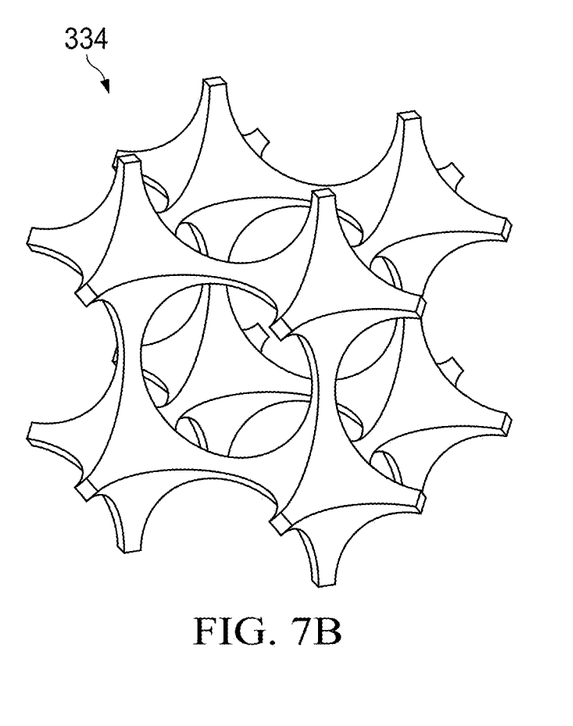
Figure 8A:
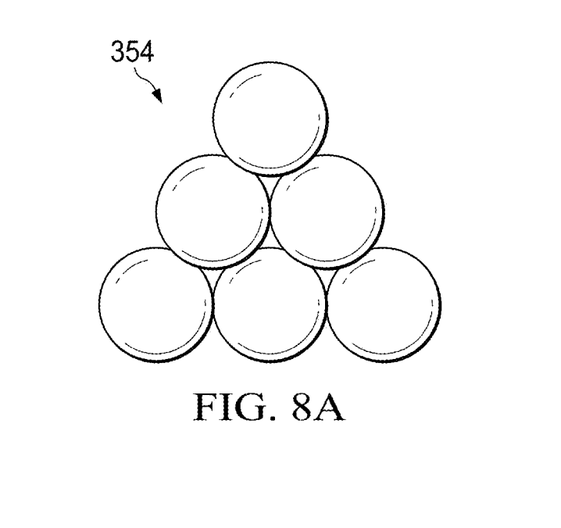
FIGS. 8A-8B are schematics of close packing opal and inverse opal structure, respectively.
Figure 8B:
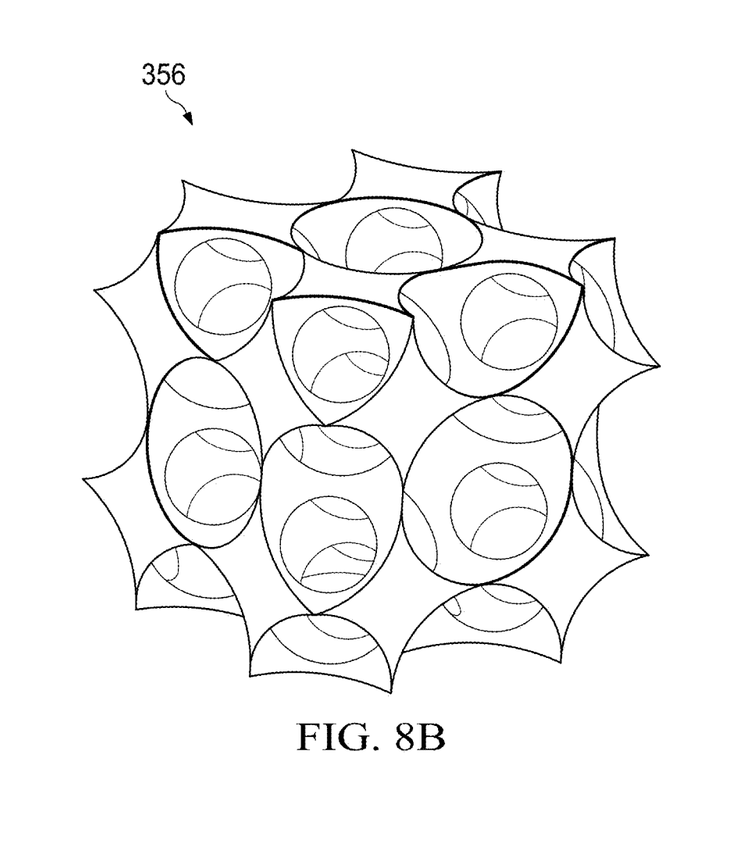

FIGS. 7A-7B are schematics of simple cubic packing opal 332 showing packing density of 52.4% and inverse opal structure 334 showing void density of 47.6%, respectively. FIGS. 8A-8B are schematic drawings of close packing opal 354 showing packing density of 70.5% and inverse opal structure 356 showing void density of 29.5%, respectively. An opal structure is a highly ordered array of colloidal spherical nanoparticles with a close-packed periodic structure (i.e., colloidal crystal). An inverse opal structure is a negative replica of the opal structure, in which the solid spheres are replaced by voids forming pores and the space between spheres is filled with new material. The opal or inverse opal structures have been used to build microdevices to manipulate fluid behaviors. As described here, calcium carbonate or calcium-magnesium carbonate are used to fill the voids of the opal structure. In the inverse opal structure, the 3D connected voids network can generate controllable porosities at the nanoscale in a microfluidic cell, while the size of voids depends on the size of the colloidal spheres template used in the fabrication. In an embodiment, a colloidal crystal with a close-packed opal structure has a packing density of spheres as 70.5%, and thus in an inverse opal structure with a void density of 70.5%.

The as described fabrication method allows common micro-flow cells to be converted to nanofluidic cells with controllable porosity at the nanometer scale, and their silica or glass surfaces were also fully converted to $CaCO_3$ or $CaMg(CO_3)_2$. The nanofluidic cell can serve as a micromodel with nanoscale porosity for carbonate reservoirs. Scanning electron micrographs were collected for confirmation.

Figure 9A:
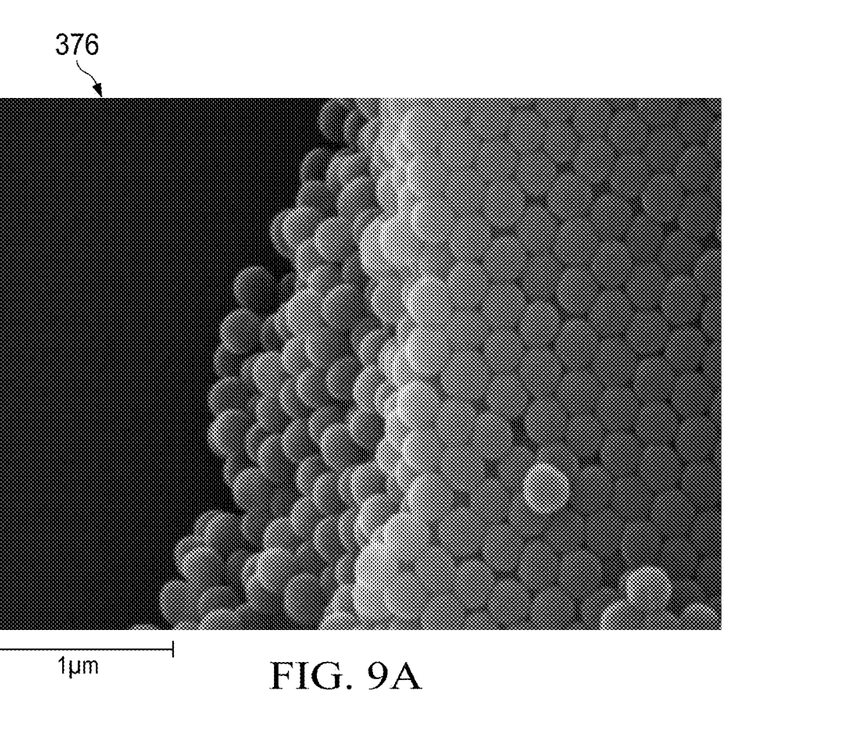
FIGS. 9A-9B are scanning electron micrographs of PS spheres and voids of calcium carbonate with nano size, respectively.
Figure 9B:
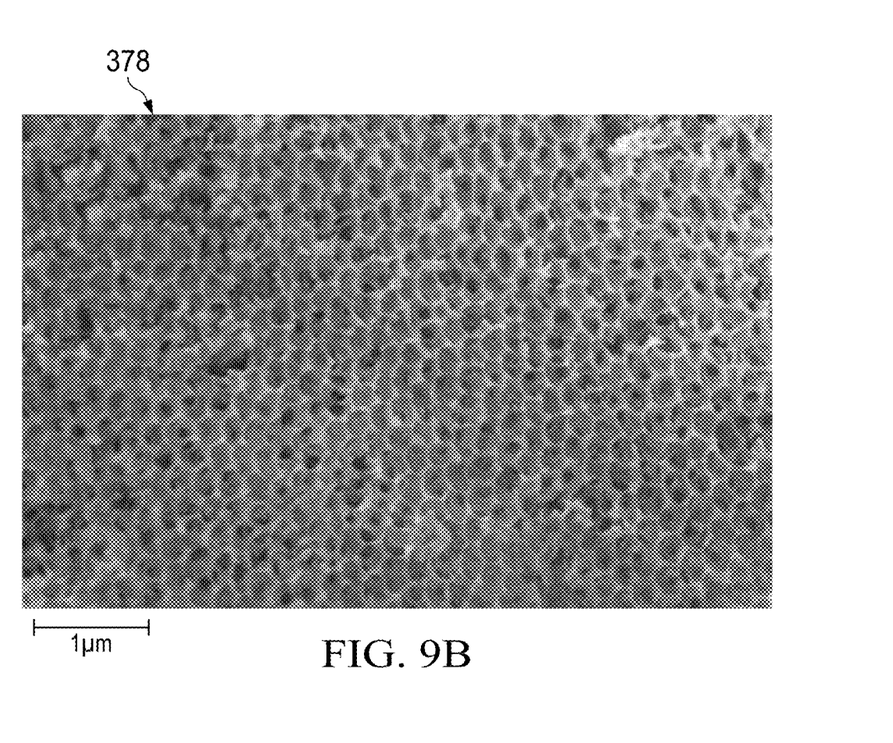

FIGS. 9A-9B are scanning electron micrographs of PS spheres 376 and voids of calcium carbonate 378 with nano size of approximately 210 nm, respectively. The SEM images were taken by scanning electron microscopy (SEM, JEOL, JSM-7100F field emission) at 3-15 kV, and no additional coating was applied onto the sample surface.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Accordingly, the previously described example implementations do not define or constrain the present disclosure. Other changes, substitutions, and alterations are also possible without departing from the spirit and scope of the present disclosure.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method for fabricating a carbonate nanofluidic structure with controllable nanosized porosity for studying fluid behaviors in an underground oil-reservoir environment, the method comprising:
   synthesizing a plurality of polymer spheres;
   purifying the plurality of polymer spheres in deionized water and redispersing the plurality of polymer spheres in a 1:1 ratio of a water-ethanol mixture;
   disposing the plurality of polymer spheres into a transparent flow cell;
   initiating crystallization of the plurality of polymer spheres to form a template with an opal structure;
   filling the transparent flow cell with a calcium-based solution and a carbonate-based solution to form nanocrystals in voids of the opal structure;
   growing an inverse opal structure of calcium carbonate or calcium-magnesium carbonate in opal structured template; and
   removing the template formed by crystallization of the plurality of polymer spheres from the transparent flow cell leaving an inverse opal structure with a plurality of nanosized pores and a carbonate surface.

2. The method of claim 1, wherein the transparent flow cell has a light path between 0.05 and 1 millimeter (mm) and a volume between 16 and 300 microliters (μL).

3. The method of claim 1, wherein the plurality of polymer spheres has a size between 50 nanometers (nm) and 1000.

4. The method of claim 1, further comprising crystallizing the plurality of polymer spheres inside the transparent flow cell by drying them at 60 Celsius (° C.) for 30 minutes.

5. The method of claim 1, wherein the calcium-based solution further comprises magnesium.

6. The method of claim 5, wherein forming the calcium-based solution comprises dissolving a solid $CaCl_2.2H_2O$ solution in deionized water as a precursor for the formation of a calcite.

7. The method of claim 5, wherein forming the calcium-based solution comprising magnesium comprises dissolving $CaCl_2.2H_2O$ and $MgCl_2.6H_2O$ solutions at 1:1 molar ratio in deionized water as a precursor for the formation of a dolomite.

8. The method of claim 5, wherein forming $CaCO_3$ or $CaMg(CO_3)_2$ crystals into the transparent flow cell includes injecting 1M $CO_3^{2-}$ into the transparent flow cell to react with the calcium or magnesium-based ions.

9. The method of claim 8, wherein forming 1M $CO_3^{2-}$ includes dissolving a $Na_2CO_3$ or $(NH_4)_2CO_3$ solution in deionized water.

10. The method of claim 8, further comprising filling the voids of the transparent flow cell with the $CaCO_3$ or $CaMg(CO_3)_2$ solution by injecting the calcium or magnesium-based solution and the $CO_3^{2-}$ solution into the transparent flow cell and drying at 150° C. for 2 hours.

11. The method of claim 1, further comprising immersing the transparent flow cell into a toluene solution overnight and dissolving the plurality of polymer spheres.

12. The method of claim 11, further comprising injecting the toluene, a chloroform, or an acetone solution into the transparent flow cell to wash the dissolved plurality of polymer spheres.

13. The method of claim 11, further comprising forming the inverse opal structure with a plurality of nanosized pores by sintering the transparent flow cell at 280° C. for 2 hours.

14. A method for fabricating a carbonate nanofluidic structure with controllable nanosized porosity for studying fluid behaviors in an underground oil-reservoir environment, the method comprising:
- disposing a plurality of polymer spheres into a transparent flow cell;
- initiating crystallization of the plurality of polymer spheres to form a template with an opal structure;
- filling the transparent flow cell with a calcium-based solution and a carbonate-based solution to form nanocrystals in voids of the opal structure;
- growing an inverse opal structure of calcium carbonate or calcium-magnesium carbonate in opal structured template;
- immersing the transparent flow cell into a toluene solution overnight and dissolving the plurality of polymer spheres; and
- removing the template formed by crystallization of the plurality of polymer spheres from the transparent flow cell leaving an inverse opal structure with a plurality of nanosized pores and a carbonate surface.

15. The method of claim 14, further comprising injecting the toluene, a chloroform, or an acetone solution into the transparent flow cell to wash the dissolved plurality of polymer spheres.

16. The method of claim 14, further comprising forming the inverse opal structure with a plurality of nanosized pores by sintering the transparent flow cell at 280° C. for 2 hours.

17. The method of claim 14, wherein the transparent flow cell has a light path between 0.05 and 1 millimeter (mm) and a volume between 16 and 300 microliters ($\mu$L).

18. The method of claim 14, further comprising synthesizing the plurality of polymer spheres.

19. The method of claim 18, further comprising purifying the plurality of polymer spheres in deionized water and redispersing the plurality of polymer spheres in a 1:1 ratio of a water-ethanol mixture.

* * * * *